United States Patent
Maier et al.

(10) Patent No.: US 7,052,914 B2
(45) Date of Patent: May 30, 2006

(54) AUTOMATED METHOD FOR EXAMINING CATALYTIC AND SPECTROSCOPIC PROPERTIES OF THE COMPONENTS OF COMBINATORIAL LIBRARIES

(75) Inventors: Wilhelm Maier, St. Ingbert (DE); Matthias Orschel, Münster (DE); Jens Klein, Heidelberg (DE); Christian Lettmann, Essen (DE); Hans Werner Schmidt, Muelheim/Ruhr (DE)

(73) Assignee: hte Aktiengesellschaft the high throughput experimentation company, Heidelberg (DE)

( * ) Notice: Subject to any disclaimer, the term of this patent is extended or adjusted under 35 U.S.C. 154(b) by 207 days.

(21) Appl. No.: 09/984,299

(22) Filed: Oct. 29, 2001

(65) Prior Publication Data
US 2002/0135753 A1 Sep. 26, 2002

Related U.S. Application Data

(63) Continuation of application No. PCT/EP00/03592, filed on Apr. 20, 2000.

(30) Foreign Application Priority Data
Apr. 27, 1999 (DE) .................. 199 18 956

(51) Int. Cl.
*G01N 31/10* (2006.01)
*G01N 1/26* (2006.01)
*G01N 33/00* (2006.01)

(52) U.S. Cl. .......... 436/37; 73/863.81; 73/863.82; 73/864.31; 73/864.73; 250/281; 250/282; 422/63; 422/64; 422/67; 422/100; 436/43; 436/54; 436/85; 436/139; 436/140; 436/141; 436/142; 436/155; 436/159; 436/161; 436/164; 436/172; 436/173

(58) Field of Classification Search ................. 73/863.81–863.82, 864.22, 864.25, 864.31, 73/864.33, 864.73; 250/281–282; 422/63–67, 422/100; 436/37, 43, 54, 85, 139–142, 155, 436/159, 161, 164, 172–173
See application file for complete search history.

(56) References Cited

U.S. PATENT DOCUMENTS

| 3,267,646 A | * | 8/1966 | Kauss et al. .................. 96/103 |
| 3,645,127 A | * | 2/1972 | Mongodin et al. ........... 73/40.7 |
| 3,926,558 A | * | 12/1975 | Davis .......................... 436/37 |
| 4,472,533 A | * | 9/1984 | Moskovits ................... 502/320 |
| 4,495,149 A | * | 1/1985 | Iwata et al. .................... 422/65 |
| 4,909,090 A | * | 3/1990 | McGown et al. ......... 73/864.33 |
| 4,988,482 A | * | 1/1991 | Weston ....................... 422/100 |
| 5,290,513 A |   | 3/1994 | Berthold et al. |
| 5,443,791 A | * | 8/1995 | Cathcart et al. .............. 422/65 |

(Continued)

FOREIGN PATENT DOCUMENTS

DE 234 941 A1 4/1986

(Continued)

OTHER PUBLICATIONS

Yao, Y.-F. Y. Journal of Catalysis 1973, 28, 139-149.*

(Continued)

*Primary Examiner*—Arlen Soderquist
(74) *Attorney, Agent, or Firm*—Jones Day (57) ABSTRACT

The invention relates to an automated method for carrying out reactions with high spatial resolution on libraries of different materials and for analysis of the products obtained using a simple robot system and an analyzer, for example a mass spectrometer.

15 Claims, 9 Drawing Sheets

U.S. PATENT DOCUMENTS

| | | | |
|---|---|---|---|
| 5,537,206 A * | 7/1996 | Akiyoshi et al. | 356/315 |
| 5,663,561 A * | 9/1997 | Franzen et al. | 250/288 |
| 5,889,199 A * | 3/1999 | Wong et al. | 73/40 |
| 5,959,297 A * | 9/1999 | Weinberg et al. | 250/288 |
| 6,063,633 A * | 5/2000 | Willson, III | 436/37 |
| 6,306,658 B1 * | 10/2001 | Turner et al. | 436/37 |
| 6,426,226 B1 * | 7/2002 | Senkan | 436/37 |

FOREIGN PATENT DOCUMENTS

| | | |
|---|---|---|
| GB | 2 237 754 A | 2/1999 |
| JP | 7-83826 * | 3/1995 |
| WO | WO 97/32208 | 9/1997 |
| WO | WO 98/15969 | 4/1998 |

OTHER PUBLICATIONS

Smigiel, W. A. et al, Industrial & Engineering Chemistry Fundamentals 1979, 18, 419-422.*
Kasemo, B. Review of Scientific Instruments 1979, 50, 1602-1604.*
Wass, J. C. et al, LC-GC 1988, 6, 420, 422-423.*
Ho, J. S. et al, American Laboratory 1989, 21, 41-2, 44, 46, 48.*
Forni, L. et al, Journal of the Chemical Society, Faraday Transactions 1992, 88, 1041-1048.*
Kapteijn, F. et al, Industrial & Engineering Chemistry Research 1993, 32, 445-452.*
Vickers, A. K. et al, Journal of Automatic Chemistry 1993, 15, 133-139.*
MacLaurin, P. et al, Analytical Chemistry 1996, 68, 1116-1123.*
Williams, C. T. et al, Journal of Catalysis 1996, 163, 63-76.*
Motohiro, T. et al, Applied Surface Science 1997, 121/122, 319-322.*
Motohiro, T. et al, Applied Surface Science 1997, 121/122, 323-326.*
Rotermund, H. H. Surface Science 1997, 386, 10-23.*
Bogdanoff, P. et al, Journal of the Electrochemical Society 1998, 145, 576-582.*
Klein, J. et al, Angewandte Chemie, International Edition 1998, 37, 3369-3372.*
Amiridis, M. D. et al, Applied Catalysis, B: Environmental 1999, 20, 111-122.*
Rodemerck, U. et al, Microreaction Technology: Industrial Prospects, Proceedings of the International Conference on Microreaction Technology, 3rd, Frankfurt, Apr. 18-21, 1999, 287-293; Editor: Ehrfeld, W., Publisher: Springer-Verlag, Berlin, Germany.*
Orschel, M. et al, Angewandte Chemie, International Edition 1999, 38, 2791-2794.*
Rodemerck, U. et al, Topics in Catalysis 2000, 13, 249-252.*
Bernd Jandeleit et al.; *Combinatorial Materials Science and Catalysis, Angew. Chem. Int. Ed.*, 1999, vol. 38, No. 17, pp. 2495-2532.
Gordon Lowe, *Combinatorial Chemistry, Chemical Society Reviews*, 1995, vol. 25, issue 5, pp. 309-317.
A. Holzwarth et al., *Detection of Catalytic Activity Combinatorial Libraries of Heterogeneous Catallysts by IR Thermography; Angewandte Chemi International Edition*; 1998, vol. 38, No. 19, pp. 2644-2647.
P. Cong et al., *High-Throughput Synthesis and Screening of Combinatorial heterogeneous Catalyst Libraries, Angewandte Chemi International Edition*, 1999, vol. 38, No. 4, pp. 484-488.
M. Reetz et al., *Time-Resolved IR-Thermographic Detection and Screening of Enantioselectivity in Catalytic Reactions, Angewandte Chemi International Edition*, 1998, vol. 37, No. 19, pp. 2647-2650.

* cited by examiner

Figure 1: example of a set-up of measuring instruments

Figure 2: assignment plan for the library of catalysts

Figure 3: schematic set-up of the library for performing and analyzing reactions Figure 4: mass spectra of the distribution of products for the reaction of propene with air over AMM-Pt$_1$Si$_1$Zr$_{20}$Al, one of the components of the library, as a function of temperature.

Figure 5: selected mass spectra showing the distribution of products for Example 2 as measured at 500°C Figure 6: product spectra obtained on selected catalyst components (amount of catalyst < 1 mg) during the oxidation of propene in air at 500°C.

AUTOMATED METHOD FOR EXAMINING CATALYTIC AND SPECTROSCOPIC PROPERTIES OF THE COMPONENTS OF COMBINATORIAL LIBRARIES

CROSS-REFERENCE TO RELATED APPLICATION

This application is a continuing application of pending PCT application PCT/EP00/03592 filed on Apr. 20, 2000, and published in German on Nov. 2, 2000 as WO00/65326. The applicants hereby claim the benefit under 35 U.S.C. 120 of this PCT application, and under 35 U.S.C. 119 of German application 199 18 956.0, filed Apr. 27, 1999. The entire contents of this PCT application and this German application are incorporated herein by reference.

BACKGROUND OF THE INVENTION

1. Field of Invention

The present invention relates to an automated method for carrying out reactions with high spatial resolution on libraries of different materials and for analysis of the products obtained using a simple robot system and an analyzer, for example a mass spectrometer.

In particular, the method relates to determining the activity and selectivity of solid or molecular materials to be used as catalysts for gas phase reactions. In an exemplary embodiment of the invention, a commercial pipetting or synthesis robot is used to position the sensor lines in order to examine reactions on a combinatorial library with high spatial resolution. The method according to the invention is characterized, in particular, by the simplicity of its set-up that is not restricted to a specific type of reactor as well as by the ease with which it is possible to switch between synthesis and screening.

2. Description of Related Art

While combinatorial chemistry has established itself as an important tool for the development of new compounds in the areas of organic, biochemical and pharmaceutical chemistry (see, e.g., the special issue: Combinatorial Chemistry, *Acc. Chem. Res.*, 1996, 29; G. Lowe, *Chemical Society Reviews*, 1995, 24(5), 309; S. R. Wilson, A. W. Czamik, *Combinatorial Chemistry—Synthesis and Application*, John Wiley & Sons, 1997), only a few examples of using combinatorial methods are known in the areas of inorganic solid state synthesis, materials research and catalyst development. The prior-art is defined by the manufacturing of libraries of materials by means of physical vapor deposition methods and by combining these methods with masking techniques, or, in the field of wet chemistry, by using ink-jet techniques, or by employing synthesis robot systems. Here, the size of libraries varies from below 100 components to 25,000 components per library. The analysis or characterization of specific properties is essential for the analysis of such libraries. Due to the dimensional miniaturization that is mandatory for the implementation of large libraries of materials, only minimal amounts of sample are available.

As of yet, only few examples are prominent with respect to the effort to record the catalytic properties of materials within combinatorial libraries of materials. The emitted heat of reaction on components of a library of catalysts can be imaged by means of IR-thermography, corrected for emissions, with spatial resolution and great sensitivity, both for gas-phase reactions with heterogeneous catalysts (A. Holzwarth, H. W. Schmidt, W. F. Maier, *Angew. Chem.* 1998, 110, 2788) and in fluid phases with enzyme catalysts (M. T. Reetz, M. H. Becker, K. M. Kuehling, A. Holzwarth, *Angew. Chem.* 1998, 110, 2792). However, using IR-thermography only allows for conclusions on the relative reactivity of the components of a library. This is insufficient whenever secondary or parallel reactions have to be taken into account, such as in the case of complete oxidation used for the search for selective oxidation catalysts. Therefore, it is desirable to have methods of analysis at hand, besides IR-thermography, that allow for the recording of chemical selectivities with high spatial resolution directly on the library, preferably in an automated manner.

The recent work of Weinberg et al. describes the application of methods of mass spectrometry for high speed scanning of libraries of catalysts (P. Cong, R. D. Coolen, Q. Fan, D. M. Giaquinta, S. Guan, E. W. McFarland, D. M. Poojary, K. Self, H. W. Turner, W. H. Weinberg, *Angew. Chem.* 1999, 111, 508; W. H. Weinberg, E. W. McFarland, P. Cong, S. Guan (Symyx Technologies), WO-A 98/15969 A2, 1998). Using mass spectrometry, Weinberg and collaborators have detected the $CO_2$ formed during the oxidation of CO with $O_2$ or NO at metallic alloys of Rh, Pd, Pt and Cu, as well as the educt gases. The system described in more detail in the aforementioned patent application relates to the spatially separated feed of educts and the removal of products via holes in the mass spectrometer and is expensive and requires significant implementation efforts. This system is specifically designed for yielding results even for the smallest amount of catalyst, down to 2–4 μg per catalyst element. This requires a costly modification of the mass spectrometer by introducing a second quadrupol filter ("ion guide") as well as the construction of a system of separated vacuum chambers for separating synthesis, sample preparation and the actual screening. Thus, a direct transfer of the library is possible from the preparation area to the mass spectrometer. However, remote handling of the sample and establishing realistic reaction conditions is exacerbated under this design. In the aforementioned publication (oxidation of CO with $O_2$ or NO to yield $CO_2$), only catalytic activities are discerned but no conclusions are possible on differences in selectivities of individual components of the library. In complex reactions with several possible products (often produced in low yield) where the products are very different or where the products have similar selectivities, this method has failed because the quantity of product is too small.

SUMMARY OF THE INVENTION

An object of the invention is to provide an improved lightweight component into which a duct can be advantageously integrated.

In accomplishing the objects of the invention, there has been provided according to one aspect of the invention a method for the automated processing of reactions on libraries of materials and for the analysis of the products created during these reactions with the aid of a robot system wherein a set of supply lines for reactants, outlet lines for reaction products, and/or signal lines are arranged in a bundle of capillaries, or that several such sets are arranged in several bundles of capillaries, with the capillaries being positioned by the robot system over individual components of a library of materials in sequence as a function of time or over several components at the same time, wherein the investigation of the library is performed with common laboratory equipment within a reactor that is not closed with respect to its environment.

According to another aspect of the invention, there has been provided a method for automated, robotic analysis of reaction products produced by reactions of libraries of materials comprising arranging a set of supply lines for reactants, outlet lines for reaction products, and/or signal lines in a bundle of capillaries; and positioning, robotically, the bundle of capillaries over individual components of a library of materials within a reactor that is not closed with respect to the environment.

In accordance with a further aspect of the invention, there has been provided a method for automated robotic analysis of reaction products produced by reactions of libraries of materials comprising providing a library of materials comprising individual components wherein each component comprises a reactant; arranging outlet lines for reaction products and/or signal lines in a bundle of capillaries; positioning, robotically, the bundle of capillaries over individual components of the library of materials; reacting a reactant of a component of the library of materials to produce a reaction product; and analyzing the reaction product with an analytical device in communication with the component of the library of materials via an outlet line of the bundle of capillaries and/or detecting the reaction product with a detector which is in optical communication with the component of said library of materials via the signal line.

Yet another aspect of the present invention provides for an apparatus for automated processing of reactions on libraries of materials and for the analysis of the products created during these reactions, comprising: a library of materials; a bundle of capillary tubes, comprising an outlet line and a supply line for supplying reactants and/or a signal line; a robot for positioning said bundle of capillary tubes over a component of said library of materials; and an analytical device in fluid communication with said component via said outlet line.

According to a further aspect of the invention, there has been provided a computer readable data storage medium having computer program code recorded thereon executable by a computer, the computer program code comprising a program code for controlling an apparatus so as to charge individual components of said library with a reactant.

Further objects, features and advantages of the present invention will become apparent from the detailed description of preferred embodiments that follows when considered together with the accompanying drawings.

BRIEF DESCRIPTION OF THE DRAWINGS

The invention is explained in detail below with reference to the exemplary embodiments and with reference to the accompanying drawings, in which.

DETAILED DESCRIPTION OF THE PREFERRED EMBODIMENTS

Surprisingly, we have found that different catalytic selectivities of materials on a library for oxidation reactions can be recorded reliably and in a fully automated manner by combining a simple analyzing device, e.g. a mass spectrometer, with a synthesis robot system. The principal advantage of the subject invention lies in the simplicity of its set-up and measurement conditions.

The components used in accordance with one embodiment of the subject invention are common laboratory equipment (pipetting robot and mass spectrometer). In this embodiment, a robot system is employed to address the individual components of the library, to supply reaction gases via supply lines, such as capillaries, to conduct measurements via signal lines, or to take up reaction products. All these inlet and outlet lines may be integrated into a bundle of capillary tubes. By way of example, for examination by mass spectrometry, the capillary bundle may solely consist of a gas supply capillary and a fine glass capillary that sucks in the mixture of product gases and that is long enough to maintain the difference in pressure between the vacuum of the mass spectrometer and the ambient pressure of the library. It has been found that a dedicated closed containment is not required for investigating the library. During the measurements, the library may, for example, be heated from below to reach the required reaction temperature. It is sufficient to cover the library with a disk that has suitable borings. The capillary bundles may be introduced into the borings, which are open at the top, by means of a synthesis robot or a suitable mechanical system. The library may then be sequentially examined while exposed to the reaction gases. By using this simple set-up, oxidation and reduction reactions on libraries have already been examined successfully and differences in selectivity of the individual components of the library have been documented reliably.

Figure 1:
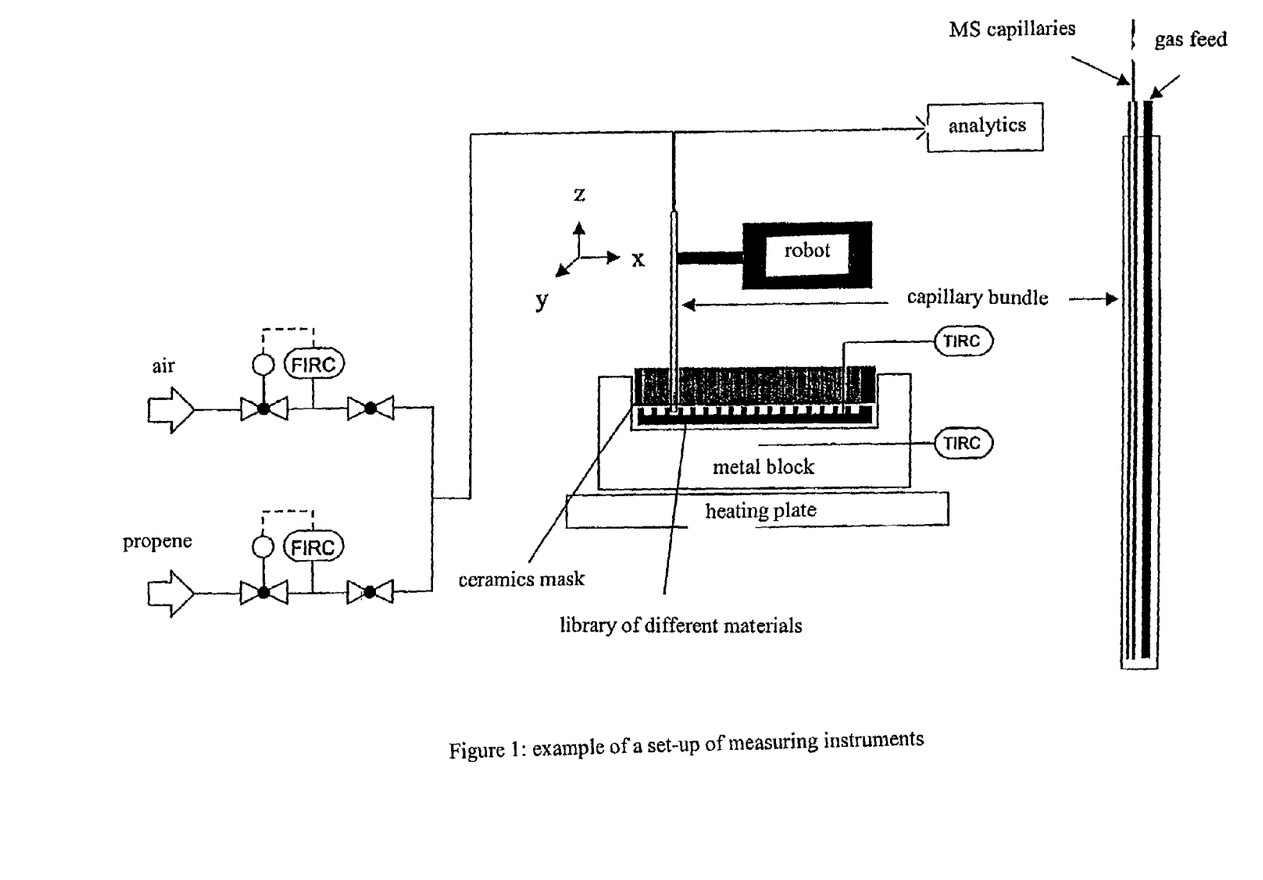
FIG. 1 depicts one example of a set-up of measuring instruments.

Example of a measuring set-up according to the invention:

FIG. 1 shows a schematic set-up for implementing one method according to an embodiment of the invention. In this embodiment, a pipetting needle of a commercially available robot is replaced by the modified capillary bundle shown on the right side of FIG. 1. This capillary bundle consists of an outer encapsulating steel capillary with the same outer diameter as the original capillary of the robot, thus enabling an effortless exchange of capillaries. Inlet and outlet lines serving as signal lines and required for supplying, monitoring and measuring the reaction are located on the inside. Depending on the manner in which the reaction is conducted, these lines may be freely chosen from among, for example, capillaries, optical wave-guides or electrical conductors. In the examples, one of the inner capillaries is used to guide the MS capillary and another one is used as an educt supply line. An optical wave-guide may be incorporated into the capillary bundle for irradiation in photo-reactions, as well as for spectroscopy analysis (IR, VIS, UV, Raman). In addition, all other methods of analysis that can be addressed by using capillaries, such as gas chromatography, HPLC, GC-MS and capillary electrophoresis, may be used for the examination of libraries of materials by incorporating suitable capillaries into the capillary bundle.

The system is designed so that it can be built into the robot's guiding system and moved to the points of the library in a fully automated manner. The temperature of the library of materials can be regulated, for example, from 20° C. to 1000° C. by heating means, such as a heating plate. Thermal radiation emanating from the substrate of the library is minimized by a ceramic mask with suitable borings. The mask lies atop the library while leaving the individual components of the library accessible due to a matching array of the holes in the mask. The borings in the ceramic hole mask on the library enable the exact positioning of the capillary bundle within the library closely above the individual components. Exact dosing of the reactants is performed with the gas supply capillary (see the right side of FIG. 1). Flexible feeding lines are used as supply capillaries as not to impede the mobility of the robot during xyz movements. The composition of the product mixture can be determined via the MS capillary and identified by suitable m/z signals. The library of materials may optionally be scanned point by point in its entirety or only a selected part of the library may be screened. This allows, for example, for a sensible combination with IR-thermography, corrected for emissions, since in this case, only the components of the library that are known for sure to be catalytically active need to be investigated for their catalytic selectivity.

In the case of the selective oxidation of propene with air on different amorphous micro-porous mixed oxide (AMM) catalysts, as shown in Example 2, the selectivities of the different active components known from the literature, have been reproduced unambiguously. This example, whose conventional realization lasted for several months in the framework of a Ph.D. thesis [H. Orzesek, University of Essen, 1998], was realized within a few hours using combinatorial techniques. This is an impressive testament to the time-saving potential inherent to working with combinatorial techniques.

An additional advantage of this measuring set-up particularly comes into play when pipetting robots are also used for building up the library of materials. In this case, the parts of the synthesis program that are specific to a spatial coordinate can also be used for the analysis (see Example 1). Switching between fully automated materials synthesis and fully automated reaction screening is accomplished by simply exchanging the capillary bundle for the pipetting capillary. In addition, the system according to another embodiment of the invention is suited for measuring more than one component at once. To this end, the capillary bundle only needs to be replaced by an array of capillary bundles. The system may also be combined with spectroscopic techniques for analysis. This allows for recording, for example, UV-, VIS-, Raman- and IR-spectra of products and of the surface of individual components within the library in-situ, i.e. during the reaction and with high temporal and spatial resolution. If an optical wave-guide is added to the capillary bundle as a probing element, it also becomes possible to perform combinatorial photo catalysis. Also, irradiation with laser light for activation of reactions, materials modification and spectroscopic characterization can be implemented easily in a set-up according to one embodiment of the invention. The method is somewhat restricted in that it does not allow for investigations under pressure. It is, however, possible to work under complete exclusion of oxygen or under inert gas conditions by enclosing the relatively small robot for synthesis in a gas-tight encapsulation, e.g. a glove-box or a plexi-glass housing.

PERFORMANCE EXAMPLES

Example 1

Manufacturing a Library for the Catalysis of Methane Oxidation

Figure 2:
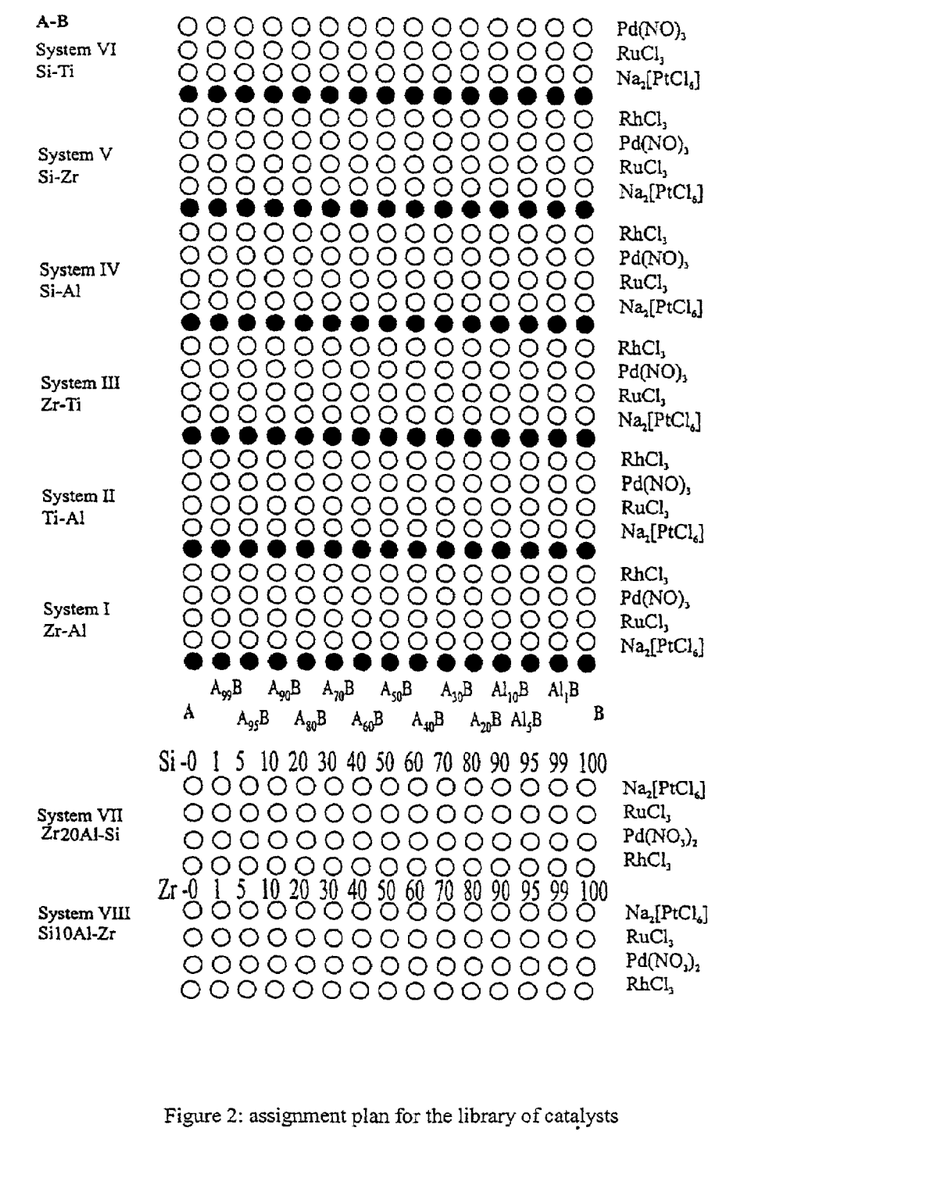
FIG. 2 depicts an assignment plan for the library of catalysts.

A slate slab (diameter: 10 cm) with 2 mm deep blind holes (diameter: 2 mm) was used as a substrate plate. It was positioned in the pipetting robot and charged with the solutions necessary for the synthesis of the catalysts. The catalyst synthesis was based the on sol-gel process. In order to protect the blind holes in the slate slab during the filling procedure, the slab was covered by suitably bored-through teflon, viton and steel disks that were fitted by means of suitable screw fixings. $SiO_2$, $TiO_2$, $ZrO_2$ and $Al_2O_3$ in varying compositions ($A_xB$) were chosen as the basic materials for the library. The alkoxy precursor compounds $Si(OEt)_4$, $Ti(O''Pr)_4$, $Zr(O''Pr)_4$ and $Al(O^{sec}Bu)_3$ were present in alcoholic solution. Pt, Pd, Ru and Rh in the form of alcoholic metal salt solutions were then used as catalytically active centers. Controlled by a computer code, a synthesis robot was used to charge the individual holes in the plate of the library with 585 sol-gel mixtures of these alcoholic solutions. The pertinent plan for assigning the positions of the library is shown in FIG. 2. The subscript in FIG. 2 represents the molar ratios of the basic oxides. The active metal content, as represented by the noble metal salts in FIG. 2, was 3 mol % for all materials. The library was pre-dried for one day at room temperature and for 2 h at 65° C. after the sol-gel components have been added in a fully automated process. The final calcination of the library (slate slab) was performed for 3 h at 250° C. after the masks have been removed.

Example 2

Investigation of the Oxidation of Methane

Figure 3:
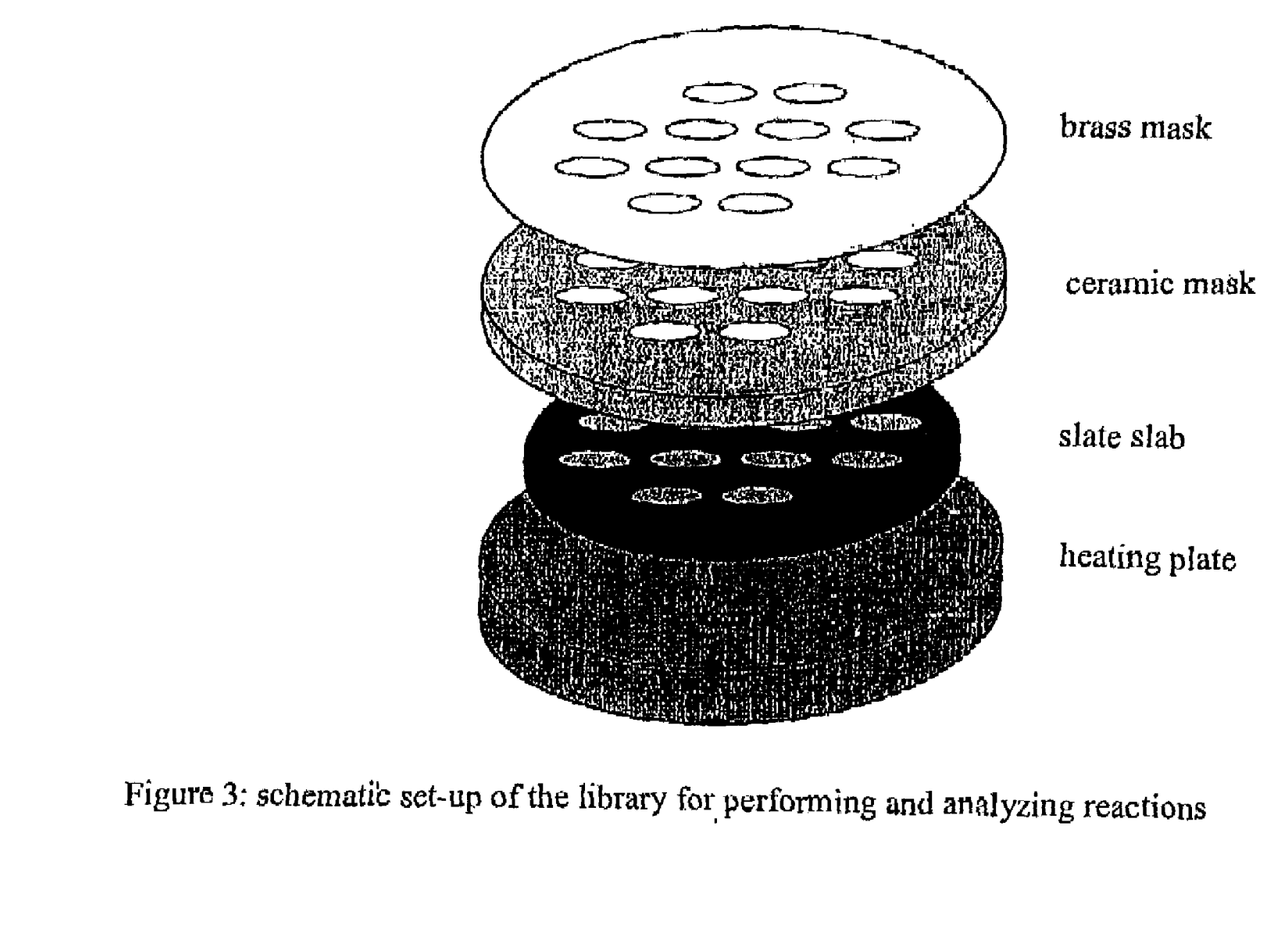
FIG. 3 depicts a schematic set-up of the library for performing and analyzing reactions.

The library of catalysts was mounted on the heating block and oriented fittingly within the pipetting robot. The library was covered by ceramic and brass masks displaying suitable through-holes (see FIG. 3). The pipetting robot was fitted with the required capillary bundle and the coordinates of the components to be investigated were retrieved from the computer code of the synthesis program.

A ratio of 0.02 for methane/synthetic air was established in the supply capillary by using a mass throughput regulator at an overall flow of 7 ml/min. The formation of the products was recorded by means of mass spectrometry using the m/z value of 44 for $CO_2$.

The materials were investigated in steps of 10 and 50 Kelvin over a temperature range from 250° C. to 600° C. While many components displayed significant activity only at temperatures above 300° C., other components were not active over the entire temperature range.

Figure 4:
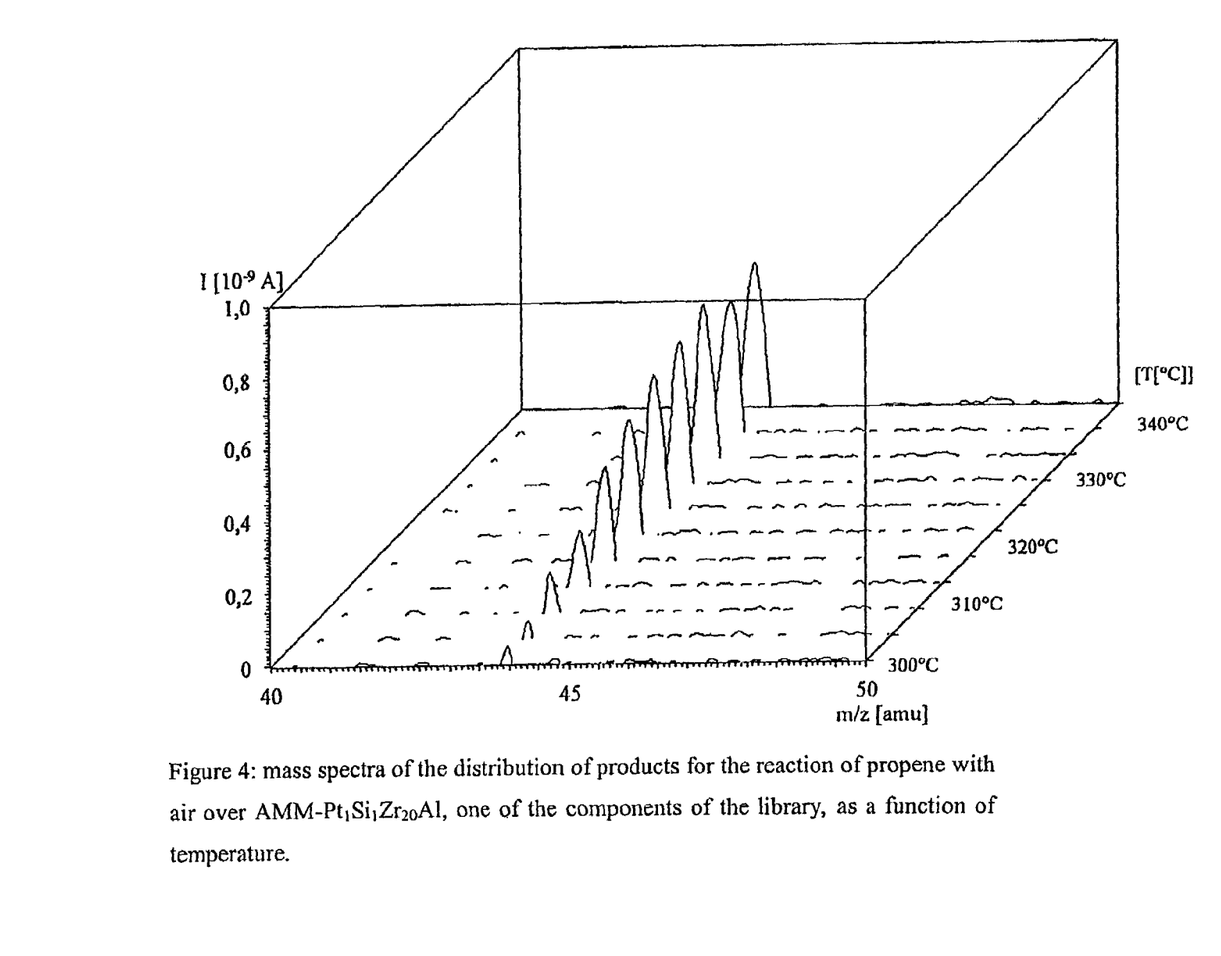
FIG. 4 depicts mass spectra of the distribution of products for the reaction of propene with air over AMM-$Pt_1Si_1Zr_{20}Al$, one of the components of the library, as a function of temperature.

FIG. 4 shows representative results as obtained from the point in the library located in row 2 and column 2 in system 7. This point relates to a ternary mixture (20 mol % $ZrO_2$, 79 mol % $Al_2O_3$, 1 mol % $SiO_2$) that contains 3 mol % $Pt^{IV}$ as the catalytically active component. The catalytic oxidation is clearly visible starting at 300° C., as indicated by the $CO_2$ peak (m/z=44), and at 320° C. the rate of formation of carbon monoxide is constant.

Example 3

Oxidation of Propene

The general procedures were as described in Example 2. Next products of complete oxidation (CO and $CO_2$), different major reaction products in different yields may be present. They can be identified by their characteristic mass signals: acrolein (m/z 56), 1,5 hexadiene (m/z=67), benzene (m/z=78) and allyl alcohol or propene oxide (m/z=58). A slate slab with 33 different AMM catalysts (2.5 mg each) was used as the library (see Table 1).

Figure 5:
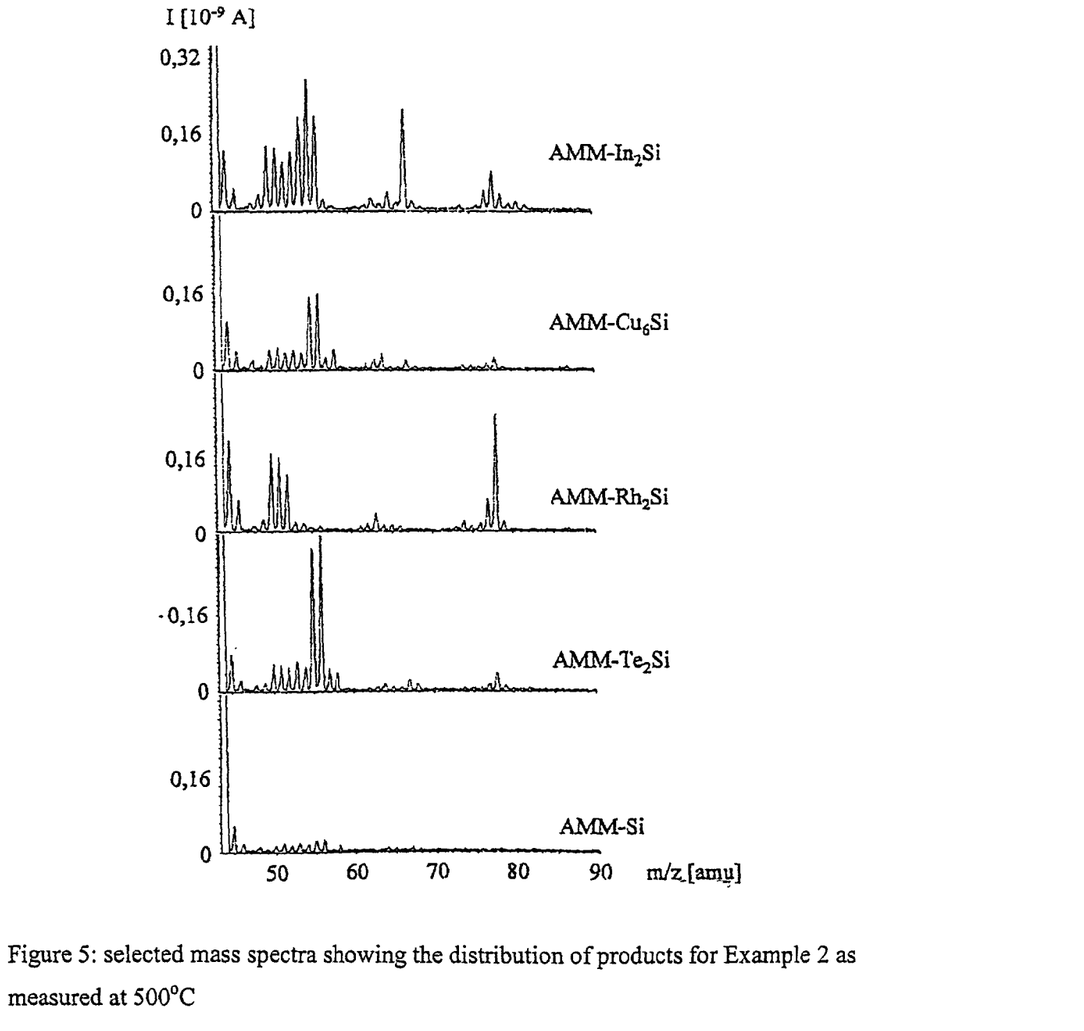
FIG. 5 selected mass spectra showing the distribution of products for Example 2 as measured at 500° C.

A ratio of 0.4 for propenelsynthetic air was established in the supply capillary by using a mass throughput regulator at an overall flow rate of 7 ml/min. The reaction was investigated at 450, 500 and 550° C. A selection of typical results is shown in FIG. 5 (500° C.). The difference in selectivity for the different catalytic materials is clearly visible. The results shown in FIG. 5 almost perfectly reproduce well-known results for the same reaction obtained in conventional flow tube reactors on the laboratory scale (approximately 500 mg catalyst mass, V/t=200 ml/min) (Orzesek, Ph.D., University of Essen, 1998; Orzesek et al. *Chem. Eng. Technol.*, in press).

TABLE 1 library of AMM catalysts*

|   | 1 | 2 | 3 | 4 | 5 | 6 |
|---|---|---|---|---|---|---|
| 1 | $Sc_2Si$ | $Y_2Si$ | $V_5Si$ | $Ta_2Si$ | $Cr_2Si$ | $Fe_2Si$ |
| 2 | $Co_2Si$ | $Rh_2Si$ | $Ni_2Si$ | $Cu_6Si$ | $Ag_2Si$ | $Au_2Si$ |
| 3 | $In_2Si$ | Si | $Sn_5Si$ | $Bi_{10}Si$ | $Te_2Si$ | $W_3Ti$ |
| 4 | $W_3Zr$ | $Mo_3Ti$ | $Mo_3Zr$ | $Sb_3Ti$ | $Sb_3Zr$ | $Cu_3Ti$ |
| 5 | $Cu_3Zr$ | $In_3Ti$ | $In_3Zr$ | $Re_3Ti$ | $Re_3Zr$ | $Cr_3Ti$ |
| 6 | $Cr_3Zr$ | $Fe_3Ti$ | $Fe_3Zr$ |   |   |   |

Example 4

Hydrogenation

Analogous to the procedure described in Example 1, components of a library of amorphous micro-porous mixed oxides (2.5 mg each) were exposed to a stream of a gas mixture of 1 ml/mm propene and 2.5 ml/min $H_2$ (at a temperature of 70° C). Mass spectrometry shows a strong signal at m/z=29 (significant for the formation of n-propane) for the mixtures AMM-$Pd_2Si$ and AMM-$Pt_2Si$. For the mixtures AMMPt$_1$Ti and AMM-Pd$_1$Ti, only a weak signal was detected. For all other components, no significant m/lz=29 signal was detected.

Example 5

Photo Catalysis

Analogous to the procedure described in Example 1, a library of $TiO_2$ photo catalysts was exposed to a stream of acetone and moist air at 30° C. In addition to the MS capillary and the gas supply line, the capillary bundle contained an optical waveguide that was used to intensely irradiate the surface of the components with light (light source: 50 W halogen lamp with focusing device, inner diameter of the optical wave-guide: 1 mm). A decay of the acetone concentration (m/z=58) that was reproducibly tied to switching on the light source was visible in the mass spectrometer.

Example 6

Oxidation of Propene as Investigated by a Doubly-Focusing Mass Spectrometer

While the gaseous products that are created in Examples 2 through 5 have been analyzed by means of a simple mass spectrometer, Example 6 elucidates the advantages of employing a mass spectrometer of higher sensitivity and resolution. For example, the simple mass spectrometer may be replaced by a doubly-focusing sector field mass spectrometer or an ion cyclotron resonance mass spectrometer (ICR-MS). Both can be employed together with the analysis robot if coupled via the capillary. The advantage of these spectrometers lies in the drastically increased sensitivity and analytical resolution. This means that it is possible to work with a much smaller amount of catalyst or with a significantly reduced overall surface area. Also, MS fragments that have the same mass but a different chemical composition, such as carbon monoxide, ethylene and nitrogen (all with m/z=28), can be resolved at base line in combinatorial experiments. The sensitivity of the measurements is high enough that glass-like catalysts, often created in robot-controlled synthesis, yield product intensities that can be measured reliably by MS even if the amount of catalyst is <0.1 mg. While only gaseous products have been analyzed in Examples 2 through 5 using a non-heated capillary, a heated capillary is employed in Example 6. This allows for detecting compounds that are difficult to volatize.

Figure 6:
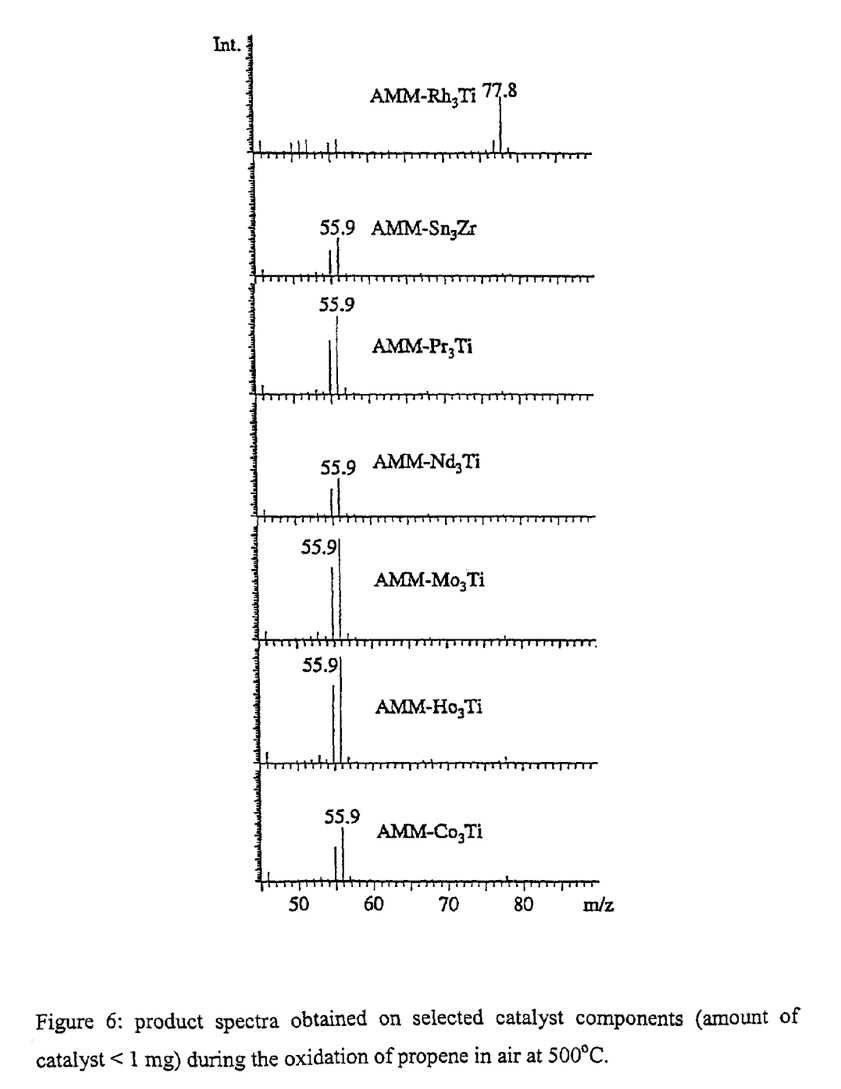
FIG. 6 depicts product spectra obtained on selected catalyst components (amount of catalyst <1 mg) during the oxidation of propene in air at 500.
Figure 7:
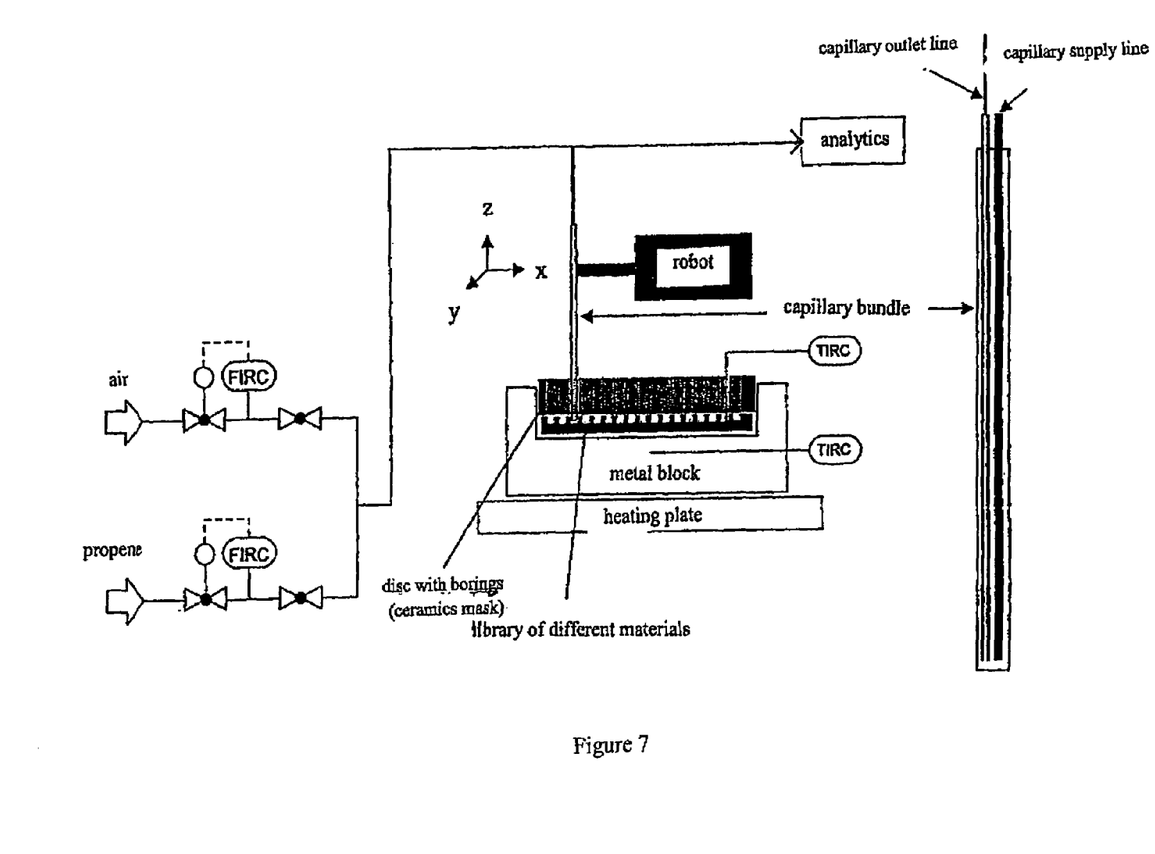
FIGS. 7–9 depict other examples of set-ups of measuring instruments.
Figure 8:
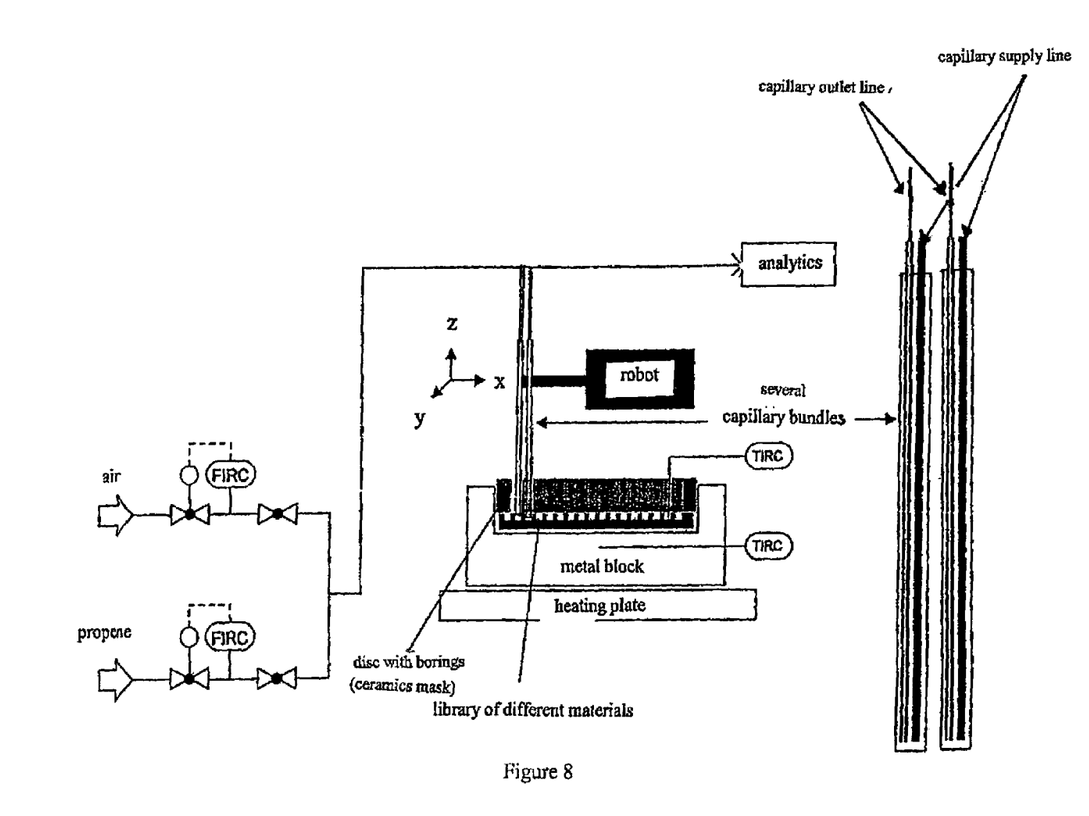
Figure 9:
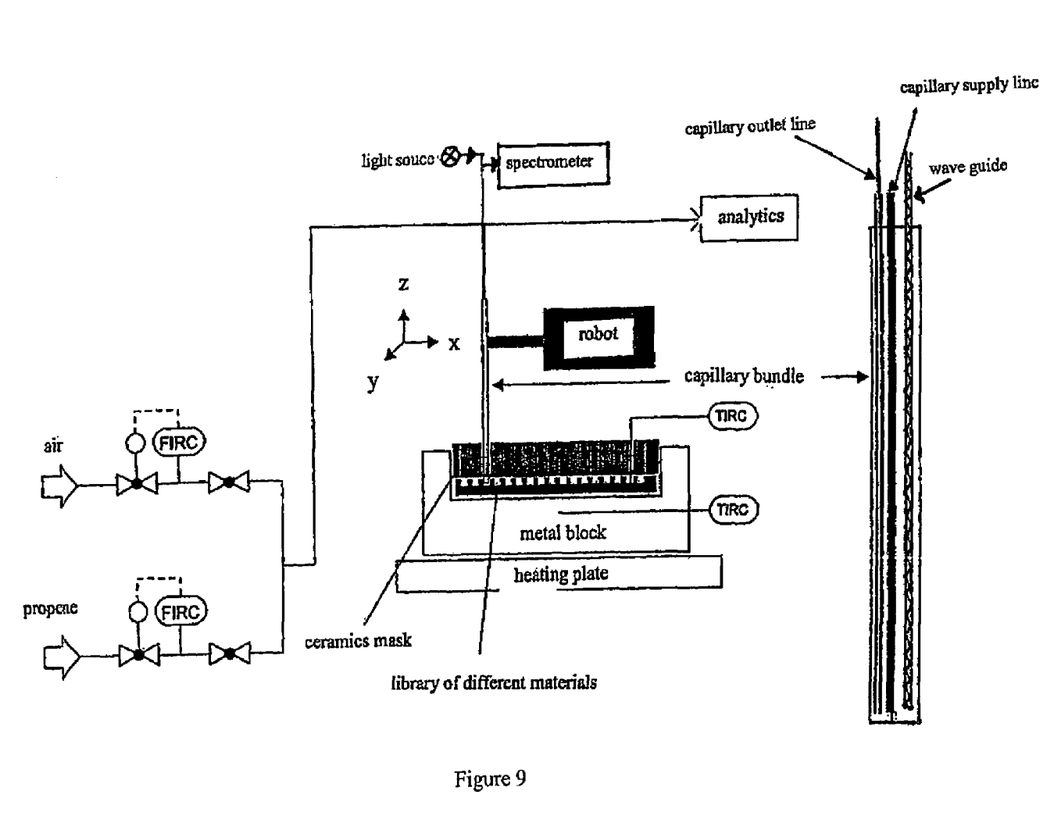

The general procedure was similar to the one described in Example 3, however, a doubly-focusing mass spectrometer (resolution up to 10,000) was used instead of the gas analysis apparatus described in Examples 1 through 5. An AMM library manufactured by robot synthesis and comparable to the one described in Example 2 was used as the library, albeit with a smaller amount of catalyst. The catalysts were not present in the form of a powder, as has been the case for Examples 1 through 5 (2.5 mg each), but as a glass-like layer with its amount ranging from 0.2–1 mg. The capillary connecting the robot with the mass spectrometer was entwined with a 2 m thermocouple (1 mm diameter) within a heat-shrinkable tube and heated up to 250° C. by applying a voltage. By heating the capillary, products that are difficult to volatize can be analyzed too. It has been found in simple tests that it is possible to detect, for example, phenol in air over a bottle containing phenol, or to detect glycol over a bottle containing glycol by using this heated capillary. Experiments with the quadrapol MS as used in Examples 1 through 5 have not resulted in detectable intensities (signal to noise ratio too low). Using selected product spectra now obtained with the sector field MS, FIG. 6 shows that acrolein (m/z=56) or benzene (m/z=78), respectively, can be formed selectively on the individual catalysts. The figure shows that catalytic activity and selectivity are discernible reliably even on the smallest amount of catalyst.

The foregoing embodiments have been shown for illustrative purposes only and are not intended to limit the scope of the invention which is defined by the claims.

What is claimed is:

1. A method comprising:
   arranging a capillary supply line and a capillary outlet line into a bundle;
   robotically positioning said bundle over individual components of a material library;
   conducting reactants through the supply line to the library components to undergo reactions; and conducting products of the reactions, while the material library is covered by a disk with bores that are open to the ambient environment from the library components through the outlet line to a mass spectrometer for the mass spectrometer to analyze the products.

2. The method of claim 1 wherein, in said robotic positioning step, said library is in a reactor that is open to the environment.

3. The method of claim 1 wherein said positioning includes sequentially positioning said bundle over individual components of said material library.

4. The method of claim 1 wherein said arranging comprises arranging several bundles, each including a capillary supply line for supplying reactants and a capillary outlet line for transferring reaction products, and said positioning includes robotically positioning said bundles over components of the library.

5. The method of claim 4 wherein said positioning includes positioning said bundles over several individual components of said material library at substantially the same time.

6. The method of claim 1, further comprising:
analyzing progress of a reaction of one of the library components as a function of time by transferring reaction products from the component to the mass spectrometer.

7. An apparatus comprising:
a material library including multiple components;
a plate that covers the library and has bores open to the ambient environment;
a mass spectrometer;
a capillary supply line configured to supply reactants to each component to undergo a reaction;
a capillary outlet line configured to conduct products of the reactions from the library components to the mass spectrometer for analysis by the mass spectrometer; and
a robot operative to position said lines sequentially over said components.

8. The apparatus of claim 7 wherein said supply and outlet lines are arranged in a bundle.

9. The apparatus of claim 7 wherein said library is in a reactor that is open to the environment.

10. A method comprising:
arranging a capillary supply line and a capillary outlet line into a bundle; and
robotically positioning the bundle over individual components of a material library;
conducting reactants through the supply line to the library components to undergo reactions; and
conducting products of the reactions, while the material library is covered by a disk with bores that are open to the ambient environment, from the library components through the outlet line to a chromatograph for the chromatograph to analyze the products.

11. The method of claim 10 wherein, in the robotically positioning step, the library is in a reactor that is open to the environment.

12. The method of claim 10 wherein the conducting products step includes conducting the products to an analytical device that is a combination of the chromatograph and a mass spectrometer.

13. The method of claim 10 wherein, during the conducting products step, the library is in a reactor that is open to the environment.

14. An apparatus comprising:
a material library including multiple components;
a disk with bores that are open to the ambient environment;
a chromatograph;
a capillary supply line configured to supply reactants to each component to undergo a reaction;
a capillary outlet line configured to conduct products of the reactions from the library components to the chromatograph for analysis by the chromatograph; and
a robot operative to position the lines sequentially over the components.

15. The apparatus of claim 14 wherein the supply and outlet lines are arranged in a bundle.

* * * * *